United States Patent [19]
Rubin

[11] Patent Number: 5,825,459
[45] Date of Patent: Oct. 20, 1998

[54] OPTICIAN'S RULER WITH SLIDING HEIGHT INDICATOR

[76] Inventor: Bruce Rubin, 120 Lucerne Blvd., Cherry Hill, N.J. 08003

[21] Appl. No.: 869,687

[22] Filed: Jun. 5, 1997

[51] Int. Cl.$^6$ .................................. A61B 3/10; A61B 3/00
[52] U.S. Cl. ............................................. 351/204; 351/200
[58] Field of Search ..................................... 351/200, 203, 351/204, 255

[56] References Cited

PUBLICATIONS

Catalog p. 21 for Measuring Instruments, Jan. 1997. Admitted prior art.
Catalog p. 18 for Vigor Optician's Rulers, Jan. 1997. Admitted prior art.
Catalog p. 67 for Hilco Optician's Rulers, Jan. 1997. Admitted prior art.
Catalog p. 42 for Ducal Trading Corp. Optician's Rulers, Jan. 1997. Admitted prior art.
Catalog pp. 165–167 for Miscellaneous Measuring Instruments, Jan. 1997. Admitted prior art.
Catalog p. 164 for Bernell Optician's Rulers, Jan. 1997. Admitted prior art.

*Primary Examiner*—Hung X. Dang
*Attorney, Agent, or Firm*—Panitch Schwarze Jacobs & Nadel, P.C.

[57] ABSTRACT

An optician's ruler having a generally elongated body having at least first and second principal surfaces, a first end, a second, opposing end, a first longitudinal edge and a second longitudinal edge is provided. An interpupillary distance scale is located on one of the at least first and second principal surfaces of the body. The interpupillary distance scale has indicia at regularly spaced intervals coinciding with standard units of measure to permit measurement of the distance between the pupils of a subject. A segment height scale is also located on one of the at least first and second principal surfaces of the body. The segment height scale has indicia at regularly spaced intervals coinciding with standard units of measure oriented generally perpendicular to the first longitudinal edge of the body. The optician's ruler may also be provided with a cross member for alignment of the segment height scale with the relevant reference point. Alternatively, a sliding indicator which includes a cross member can be moved along the segment height scale to accurately measure from the bottom of the lens to the desired reference point on the wearer's eye.

21 Claims, 2 Drawing Sheets

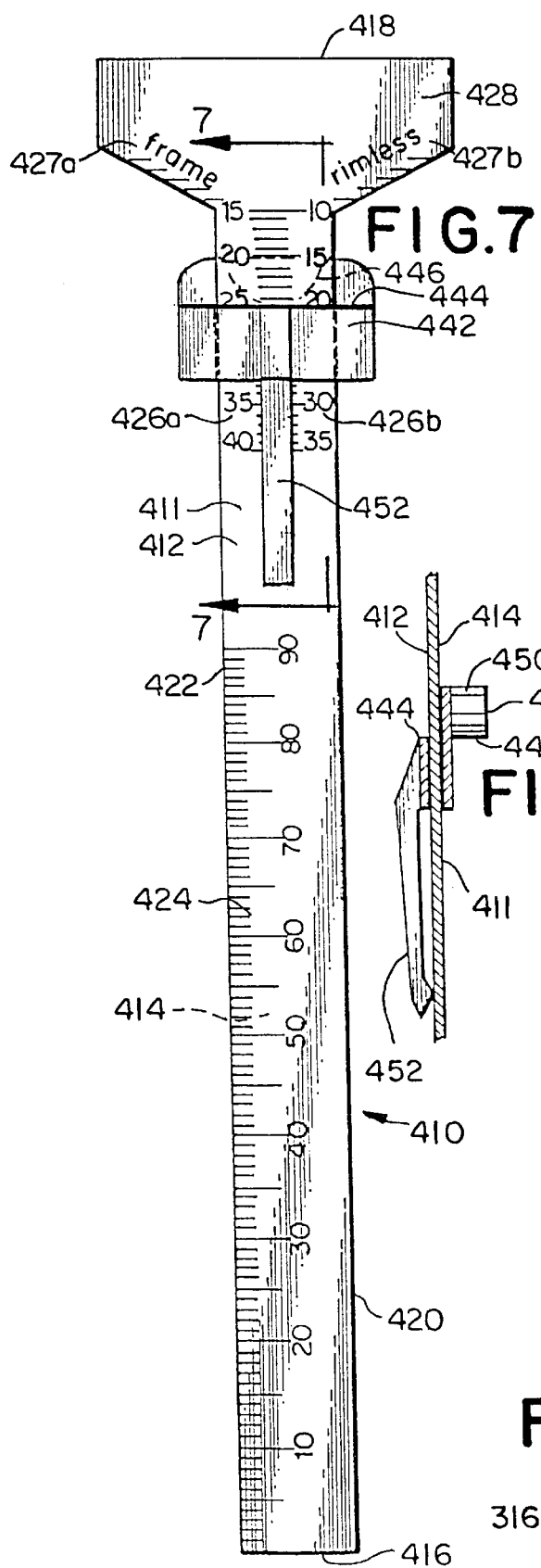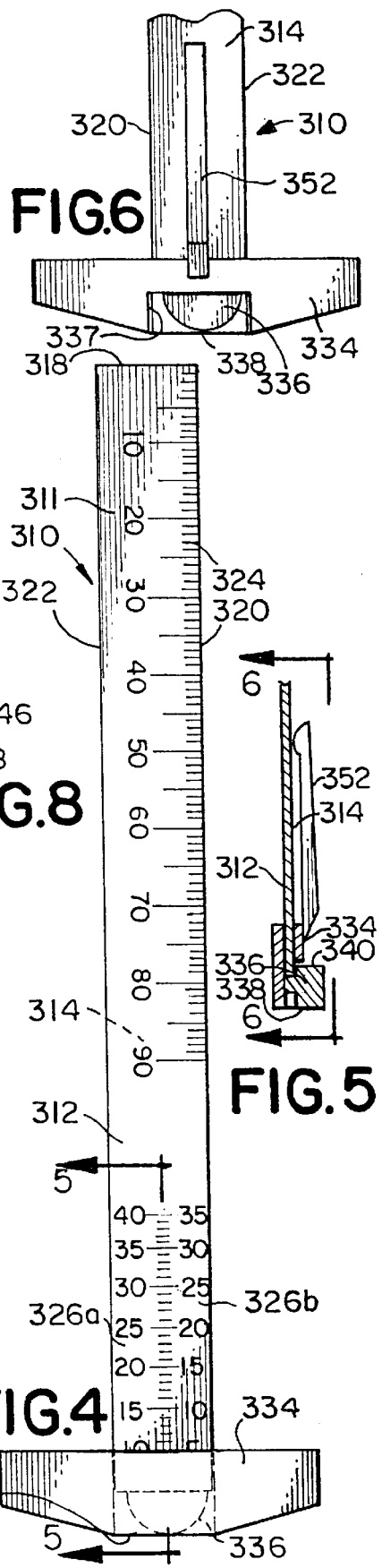

OPTICIAN'S RULER WITH SLIDING HEIGHT INDICATOR

BACKGROUND OF THE INVENTION

The present invention relates generally to an optician's ruler, and more particularly to a single optician's ruler having both an interpupillary distance scale and a separate segment height scale.

To fit a pair of eyeglasses to an individual wearer, an optician or other health professional must measure the distance between the individual's pupils to determine the proper placement of the lenses within the frame. Optician's generally measure the individual's interpupillary distance with a pocket ruler, holding the ruler generally horizontally before the face of the individual, aligning the left end of the ruler with the left edge of the individual's right cornea and noting the distance along the scale to the left edge of the left cornea.

In addition, individuals often require eyeglasses having multi-focal lenses, either in the form of bifocal lenses, trifocal lenses, progressive lenses, or the like. To fit a pair of multi-focal eyeglasses to an individual, the optician must determine the correct vertical placement of the top edge of the multifocal segment relative to the eye of the individual. This measurement is generally referred to as the segment height measurement. To measure segment height, the desired eyeglass frame is worn by the individual and the optician holds a ruler, vertically oriented, before the face of the individual and measures the distance from the lowest point within the eyeglass frame to a level equal to a point relative to the individual's eye. Depending on the type of multifocal lens to be used, this level will be generally at the lowest point of insertion of the lashes of the lower eyelid, the point halfway in between the lower edge of the pupil and lower edge of the cornea, or the point directly in front of the center of the pupil.

Because an optician holds the ruler in a horizontal orientation for measuring an individual's interpupillary distance and holds the ruler in a vertical orientation when making the segment height measurement, a ruler having a single scale is unsatisfactory because the numerals are laid out in only a single direction. The prior art overcomes this shortcoming by providing a ruler with multiple scales including a separate height scale. However, this previous design incorporates a clear plastic scale printed in white which is difficult to see. Additionally, it does not provide an unobstructed view of the wearer's eye. This makes the ruler more difficult to use. As with every optician's ruler available today, this one has a PD scale which runs the length of the ruler. The reason this is a problem, is that it does not leave room for both sides of the segment height scale. In order to be effective, it is sometimes necessary to measure each eye individually for segment heights. The invention allows easy unobstructed measuring for either a right or a left eye. Another previous design also incorporates a clear plastic scale that temporarily clips into the eyeglass frame where the lens would be positioned. This design is equally difficult to see through. Additionally, in order to use this device to measure an individual, the measurer would be required to have two separate rulers because this device can not be used to measure the interpupillary distance.

An additional problem that exists in the prior art concerns how measurements of segment height are performed. Determination of the segment height measurement requires the optician to ensure that the eyeglasses are situated properly on the individual's face while concurrently holding the ruler with an outstretched arm, aligning the ruler with the relevant point on the eyeglasses and determining the level on the ruler with which the reference point is aligned. Because proper alignment of the lenses relative to the individual's eye is essential, accuracy and consistency in this measurement are of primary concern. However, opticians often encounter difficulty in concurrently aligning a ruler with two separate reference points—the location of the low point of the lens and the position relative vertically to the wearer's eye. Moreover, the results of a segment height scale measurement may be inaccurate because in some cases the optician must "draw" an imaginary line through the reference point and the ruler. Additional inaccuracy is introduced because the optician has no means by which to mark the measurement on the ruler, thereby making it difficult for the optician to ensure proper alignment of the ruler, the eyeglasses, and the patient's eyelid while taking a measurement from the ruler.

The present invention overcomes the problem of the prior art by providing an interpupillary distance scale and a segment height scale on the same ruler. By having a single ruler with a first scale configured for horizontal reading and a second scale configured for vertical reading, the optician can quickly and efficiently move from making an interpupillary distance measurement to a segment height measurement without reaching into a pocket or otherwise retrieving a separate second ruler. The invention also overcomes the problem of "drawing" an imaginary line by incorporating a cross member which is wider than the body of the ruler. This cross member can either be fixed or movable with respect to the body of the ruler.

Another prior art ruler addresses the imaginary line problem by incorporating a cross member as a part of the body of the ruler. This scale also has its numbers oriented diagonally, making it more difficult to use. Another problem with this ruler is that it only has a single scale and does not provide the unobstructed view necessary for measuring interpupillary distances.

Another problem with all known prior art is that there is no way to ensure that the measurement for segment heights begins exactly at the lowest point of the lens to be mounted in the eyeglass frame. The invention overcomes this problem by incorporating a stop member at a precise point on the ruler which corresponds to the zero point of the scale. In another configuration, the stop member is fixed to a movable indicator. This version of the invention also helps to ensure that the segment height measurement is taken from the lowest point of the frame. In a case where the lenses will be mounted in a "rimless" frame, the opposing end of the stop member may be used to take an outside measurement of a demonstration lens, as opposed to the inside measurement of the frame.

BRIEF SUMMARY OF THE INVENTION

Briefly stated, the present invention provides an optician's ruler having a generally elongated body having at least first and second principal surfaces, a first end, a second, opposing end, a first longitudinal edge and a second longitudinal edge. An interpupillary distance scale is provided on one of the at least first and second principal surfaces of the body. The interpupillary distance scale has indicia at regularly spaced intervals coinciding with standard units of measure to permit measurement of the distance between the pupils of a subject. A segment height scale is provided on one of the at least first and second principal surfaces of the body. The segment height scale has indicia at regularly spaced intervals coinciding with standard units of measure oriented generally perpendicular to the first longitudinal edge of the body.

In another aspect, the present invention provides an optician's ruler having a generally elongated body with at least first and second principal surfaces, a first end, a second end, and a longitudinal axis. A segment height scale is located on one of the at least first and second principal surfaces of the body. The segment height scale includes indicia at regularly spaced intervals coinciding with standard units of measure to permit measurement of the height of a segment of a multi-focal lens. An indicator device is supported by and movable with respect to the body. The indicator device includes an indicator for alignment with the segment height scale indicia and a stop member for engaging a pair of eyeglasses.

In another aspect, the present invention provides an optician's ruler having a generally elongated body having a first and second principal surfaces, a first end, a second end, and a longitudinal axis extending between the ends. A segment height scale is provided on a principal surface of the body. The segment height scale has indicia at regularly spaced intervals coinciding with standard units of measure to permit measurement of the height of a segment of a multi-focal lens. An indicator device is supported by and movable with respect to the body. The indicator device includes an indicator for alignment with the segment height scale indicia. A stop member is connected to a principal surface of the body for engaging a pair of eyeglasses.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 4 is an elevational view of a fourth embodiment of a dual scale optician's ruler in accordance with the present invention;

FIG. 5 is a cross-sectional view taken along lines 5—5 in FIG. 4;

FIG. 6 is a rear elevational view taken along lines 6—6 in FIG. 5;

FIG. 7 is an elevational view of a fifth embodiment of a dual scale optician's ruler in accordance with the present invention; and FIG. 8 is a cross-sectional view taken along lines 8—8 in FIG. 7.

DETAILED DESCRIPTION OF THE INVENTION

Figure 1:
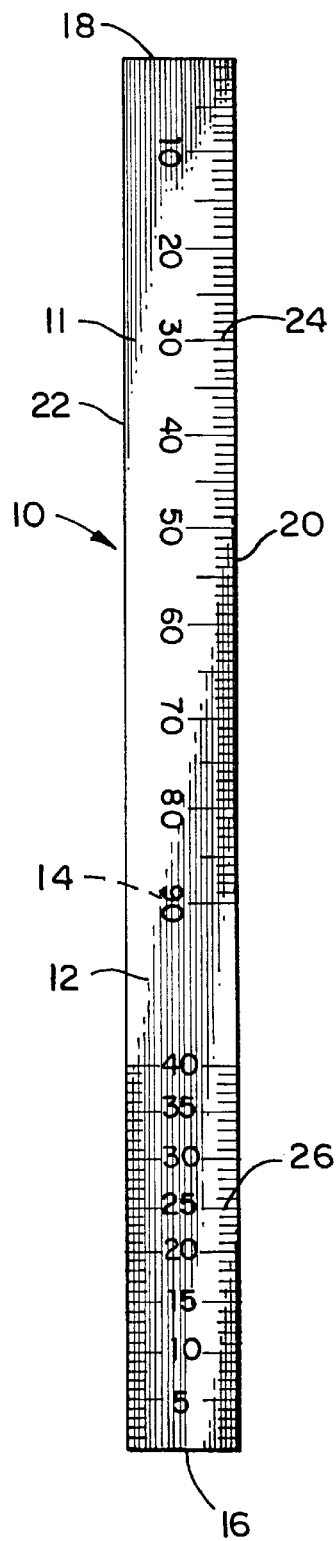
FIG. 1 is an elevation view of a dual scale optician's ruler in accordance with a first embodiment of the present invention.

Certain terminology is used in the following description for convenience only and is not limiting. The words "right," "left," "lower," and "upper," designate directions in the drawings to which reference is made. The words "inwardly" and "outwardly" refer to directions toward and away from, respectively, the geometric center of the optician's ruler and designated parts thereof. The terminology includes the words above specifically mentioned, derivatives thereof and words of similar import.

Referring to the drawings in detail, wherein like numerals are used to indicate like elements throughout, there is shown in FIG. 1 an optician's ruler 10, in accordance a first embodiment of the present invention. The ruler 10 includes an elongated body 11, which, in the present embodiment is generally flat, providing a generally rectangular shape in elevation view as well as in plan view (not shown). However, the body 11 need not be flat, and may have a shape which, in plan view, comprises virtually any two-dimensional geometric shape, including square, circular, or elliptical, without departing from the spirit and scope of the invention.

The body 11 includes a first principal surface 12, an opposing second principal surface 14, a first end 16, an opposing second end 18, a first longitudinal edge 20 and an opposing second longitudinal edge 22. In the first preferred embodiment, the body 11 is approximately six inches long, one-half of an inch wide, and one-sixteenth of an inch thick. Other physical dimensions may also be used with equal efficacy.

The ruler 10 may be made from virtually any structural material that provides sufficient rigidity to enable a user to measure the distance between a subject's pupils and to measure the height of a segment of a multi-focal lens. Materials that may be employed in the construction of the ruler 10 include, but are not limited to, metals, polymer materials, especially thermoplastic or thermosetting polymers, composite materials, and wood. In the first preferred embodiment the ruler 10 is constructed of plastic.

The ruler 10 includes an interpupillary distance scale 24, located on the first principal surface 12 of the body 11 and proximal to the second end 18. It will be appreciated by those of ordinary skill in the art that the interpupillary distance scale 24 need not be on the first principal surface 12, nor proximal to the second end 18, but may be located at any convenient place on either the first principal surface 12 or the second principal surface 14.

The interpupillary distance scale 24 has indicia at regularly spaced intervals which coincide with standard units of measure to permit measurement of the distance between the pupils of a subject. In the present embodiment, the indicia are inscribed onto the first principal surface 12 of the body 11, but may also be applied by any other appropriate means, such as by printing, painting, chemical or physical etching, or they may be formed during molding or other fabrication of the body 11. The units of measurement in the present embodiment are metric, broken down into one millimeter increments, although any other standard units of measure may alternatively be employed. The interpupillary distance scale 24 in the present embodiment begins at the second end 18 and extends along the first longitudinal edge 20 a distance of ninety millimeters, however, it will be appreciated by those skilled in the art that the interpupillary distance scale 24 could extend for a greater or lesser length and need only extend for a length sufficient to measure the distance between a subject's pupils.

The indicia on the interpupillary distance scale 24 are comprised of a combination of lines and numerals, although other means of indicating distance, such as lines, numerals, or other symbols, alone or in combination, may be employed. (Each line originates proximal to a point either near or on the first longitudinal edge 20 of the body 11 and extends generally perpendicularly with respect to the first longitudinal edge 20 across a portion of the first principal surface 12 of the body 11. The lines are all of approximately the same length with the exception of longer lines located at five millimeter increments beginning at the end of the interpupillary distance scale 24 proximal to the second end 18 of the body 11.

The numerals of the interpupillary distance scale 24 are located adjacent to the corresponding lines, are oriented generally parallel to the first longitudinal edge 20 of the body 11, and are oriented for convenient reading when the ruler 10 is held by the optician or other user with the first longitudinal edge 20 upwardly. Numerals are included on the ruler 10 in ascending numeric order beginning at the second end 18 of the body 11 and are provided at ten millimeter increments, beginning at the second end 18.

The present embodiment also includes a segment height scale 26 which is also preferably positioned on the first a principal surface 12 of the body 11 and is disposed proximate to the first end 16 of the body 11. It will be appreciated by those of ordinary skill in the art that the segment height scale 26 need not be on the first principal surface 12, nor proximate to the first end 18, nor on the same principal surface as the interpupillary distance scale 24, but may be located at any position on either the first principal surface 12 or second principal surface 14.

The segment height scale 22 has indicia at regularly spaced intervals coinciding with standard units of measure, to permit measurement of the height of a segment of a multi-focal lens or the placement of a progressive lens relative to a patient's eye. The units of measurement in the present embodiment are metric, broken down into one millimeter increments, although any other standard units of measure may be employed. In the present embodiment, the segment height scale 26 begins at the first end 16 and extends toward the second end 18 for a distance of forty millimeters. It will be appreciated by those of ordinary skill in the art, however, that the segment height scale 22 may extend for a greater or lesser distance and need only extend for a length sufficient to measure the height from a position corresponding with the bottom of a lens to the lowest insertion point of the eyelashes on the individual's eyelid. In the present embodiment, the segment height scale indicia are inscribed onto the first principal surface 12 of the body 11, but may also applied by any other appropriate means, such as by printing, painting, chemical or physical etching, or they may be formed during casting or other fabrication of the body 11.

The indicia of the segment height scale 26 are comprised of both lines and numerals, although other means of indicating distance, such as lines, numerals, or other symbols, either in combination or alone, may be employed. Each line in the segment height scale 26 extends inwardly from the first and second longitudinal edges 20, 22, generally perpendicular thereto, but does not traverse the entire first principal surface 12 of the body 11, leaving a central channel therebetween for the placement of the numerals. The lines are all of approximately the same length with the exception of longer lines located at five millimeter increments beginning at the end of the segment height scale 26 proximal to the first end 16 of the body 11.

The numerals of the segment height scale 26 are located between the corresponding lines of the segment height scale 26, are oriented generally perpendicular to the first longitudinal edge 20 of the body 11, and are oriented for reading when the ruler 10 is held by the optician or other user with the second end 18 of the body 11 upwardly. In the present embodiment only numerals corresponding with distance in five millimeter increments from the first end 16 of the body 11 are included and are arranged in ascending numeric order beginning from the first end 16. This configuration of the lines and numerals is intended to be exemplary and is not intended to be limiting as it is appreciated by those of ordinary skill in the art that other line configurations, such as extended lines and corresponding numerals at ten millimeter increments, will be equally effective.

In practice, an optician or other user utilizes the present embodiment of the invention to perform both interpupillary distance and segment height measurements using a single ruler 10. To perform an interpupillary distance measurement, the optician holds the ruler 10 in a horizontal orientation with the first longitudinal edge 20 upwardly and generally aligned with the edges of the corneas of the individual. The ruler 10 is held before the face of the individual with the zero point 18 of the body 11 aligned with the left edge of the right cornea of the individual. The optician or other user then reads the distance on the interpupillary distance scale 24 to the left edge of the individual's left cornea.

To measure the segment height of a multi-focal lens using the present embodiment, the individual dons the eyeglass frames into which the lens will ultimately be fit. The optician faces the individual and holds the ruler 10 by the second end 18 from above the eye of the individual with the first end 16 extending downwardly before the eye of the individual. The first end 16 is aligned with the lens mounting surface on the portion of the eyeglass frame that embraces the lower periphery of the lens and the optician determines the vertical height from the lens mounting surface to the level equal to the desired reference point relative to the eye of the individual. Alternatively, if the eyeglass frame is of the type that does not surround the lower periphery of the lens, the optician measures the distance from the lower periphery of a demonstration lens to the same point relative to the eye of the individual. This measurement provides the optician with the vertical positioning of a multi-focal lens within the eyeglass frame.

Figure 2:
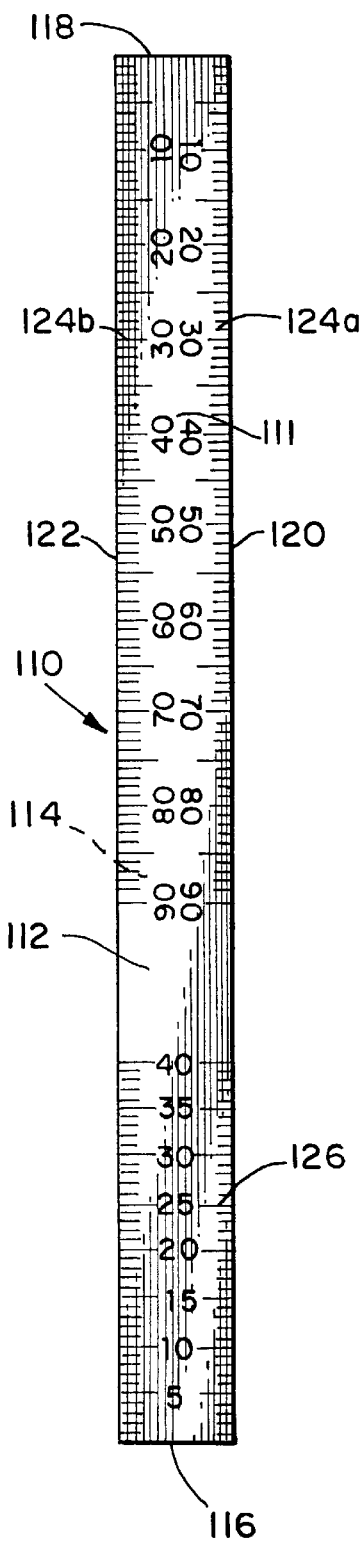
FIG. 2 is an elevational view of a dual scale optician's ruler in accordance with a second embodiment of the invention.

Referring now to FIG. 2, a second preferred embodiment 110 of an optician's ruler is shown. The second embodiment 110 is similar to the first embodiment 10, and like numbers with the hundreds digit "1" have been used to describe like elements. For example, the first longitudinal edge 120 of the second embodiment is similar to the first longitudinal edge 20 of the first embodiment, and accordingly a detailed description of these similar features is not believed to be necessary. The differences between the second embodiment 110 and the first embodiment 10 are described in detail below.

In the second preferred embodiment 110, interpupillary distance scales 124a, 124b are provided along the first and second longitudinal edges 120, 122, respectively. The numerals on the interpupillary distance scale 124a along the first longitudinal edge are oriented to be readable when the first longitudinal edge 120 is oriented upwardly. The numerals along the interpupillary distance scale 124b are oriented to be readable when the second longitudinal edge 122 is oriented upwardly. This allows the ruler 110 to be easily used by left-handed or right-handed optician's or other users to measure the interpupillary distance of a patient.

Both interpupillary distance scales 124a, 124b begin at the second end 118 and extend along the respective first and second longitudinal edges 120, 122 a distance of ninety millimeters. However, it will be appreciated by those skilled in the art that the interpupillary distance scales 124a, 124b could extend for a greater or lesser length and need only extend for a length sufficient to measure the distance between a subject's pupils.

Figure 3:
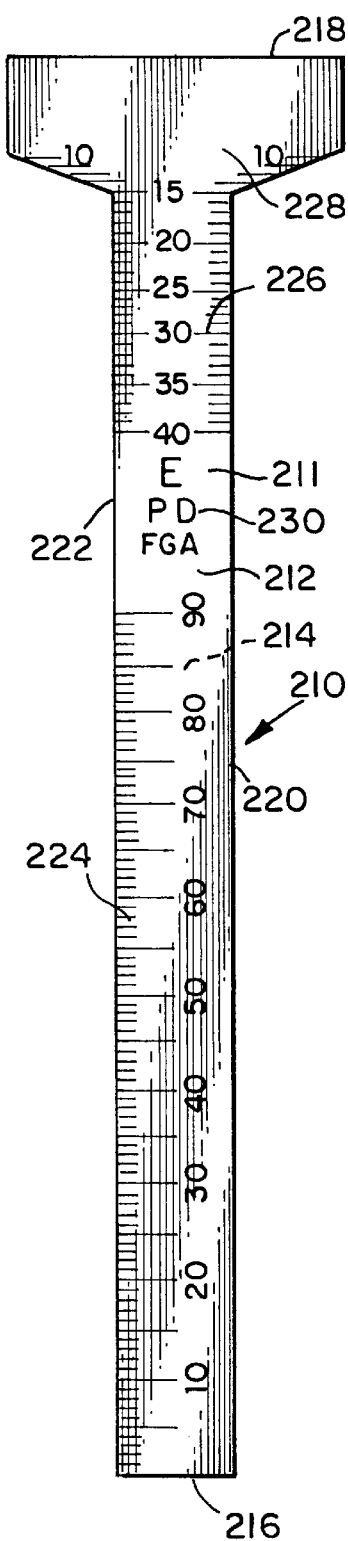
FIG. 3 is an elevational view of a dual scale optician's ruler in accordance with a third embodiment of the present invention.

Referring now to FIG. 3, a third embodiment of an optician's ruler 210 is shown. The third embodiment of the optician's ruler 210 is similar to the first embodiment 10, and like numbers with the hundreds digit "2" have been used to describe like elements. For example, the interpupillary distance scale 224 of the third embodiment is similar to the interpupillary distance scale 24 of the first embodiment, and accordingly a detailed description of these similar features is not believed to be necessary. The differences between the third embodiment 210 and the first embodiment 10 are described in detail below.

In the third preferred embodiment 210, the interpupillary distance scale 224 is located in proximity to the first end 216 and is oriented such that the characters are readable when the second longitudinal edge 222 is oriented in the upward direction. The segment height scale 226 is located in proximity to the second end 218, and the characters on the segment height scale 226 are readable when the second end 218 is oriented upwardly.

A cross member 228 is provided as an integral part of the ruler 210 along the second end 218 in order to allow the user to more accurately measure the segment height by aligning the second end 218 with the level equal to the desired reference point relative to the eye of the individual and reading the distance to the bottom of the lens. The cross member 228 is wider than the remainder of the body 211 to facilitate alignment with the reference point, since the lowermost portion of the frame usually is not aligned with the central region of the patient's eye, and providing the cross member 228 allows the measurement to be taken directly, instead of trying to align the measurement with a feature which is not directly aligned with the scale.

Preferably, an eye chart 230 is located on the ruler 210 between the interpupillary distance scale 224 and the segment height scale 226. The characters of the eye chart 230 are arranged such that they are legible when the second end 218 of the ruler 210 is oriented upwardly, and the characters are sized in a manner known to those skilled in the art with rows of characters having differing sizes in order to allow an optician or other user to determine near point visual acuity of a patient.

Referring now to FIGS. 4–6, a fourth embodiment of an optician's ruler 310 is shown. The fourth embodiment of the optician's ruler 310 is similar to the first embodiment 10, and like numbers with the hundreds digit "3" have been used to describe like elements. For example, the interpupillary distance scale 324 of the fourth embodiment 310 is similar to the interpupillary distance scale 24 of the first embodiment, and accordingly a detailed description of these similar features is not believed to be necessary. The differences between the fourth embodiment 310 and the first embodiment 10 are described in detail below.

In the fourth preferred embodiment 310, a sliding cross member 334 is slidably disposed on the body 311 of the ruler 310 in proximity to the segment height scale 326. Preferably, a stop member 336 is attached to the second principal surface 314 of the body 311 in proximity to the first end 316 for engaging a pair of eyeglasses and to prevent the cross member 334 from sliding off the first end 316. Preferably, the slidable cross member 334 includes a recess 337, best shown in FIG. 6, which allows the cross member 334 to slide down and around the stop member 336 to a lowermost position.

The stop member 336 is preferably semi-circular in form and includes a first rounded surface 338 for engaging a lens mounting surface of the pair of eyeglasses, and a second relatively flat surface 340 which is used for engaging a peripheral surface of a lens of a pair of rimless eyeglasses.

As shown in FIGS. 5 and 6, preferably a clip 352 is attached to the cross member 334 in order to allow the ruler 310 to be clipped to an object, such as a user's pocket. Preferably the clip 352 is resilient and provides a clamping force between the body 311 and the clip 352 to retain the ruler 310 in a desired position. Preferably, the cross member 334 and the clip 352 are formed from a metallic or polymeric material, and may be molded or otherwise formed as a unitary part having the desired shape. However, it will be recognized by those skilled in the art from the present disclosure that the clip 352 may be made as a separate piece which is attached to the indicator device by a subsequent operation, such as bonding, crimping or welding.

In the fourth preferred embodiment, the cross member 334 engages the body 311 with a frictional sliding fit such that the cross member 334 remains in a selected position on the body 311 until a force is applied on the cross member 334 by a user to adjust the cross member position for measuring a segment height. Alternatively, a thumb wheel screw (not shown) or a set screw may be installed in the cross member 334 to act upon the body 311 to keep the cross member in a desired position.

For segment height measurements, the first surface 338 of the stop member 336 is set on the inside bottom of the glasses frame, or in the case of rimless glasses, the second surface 340 of the stop member 336 is hooked on the bottom edge of the lens. The user slides the cross member 334 upwardly on the body 311 until the cross member 334 is aligned with the level equal to the desired reference point relative to the eye of the individual to measure the segment height. The height is read from the indicia on one of the first and second height scales 326a, 326b, along the upper side of the cross member 334. Segment height scales 326a, 326b are printed in different colors preferably black for segment height scale 326a for inside frame measurements and red for segment height scale 326b for rimless outside measurements. These numbers will correspond to either the top or bottom of the stop member 336 accordingly.

Referring now to FIGS. 7 and 8, a fifth embodiment of an optician's ruler 410 is shown. The fifth preferred embodiment 410 is similar to the third preferred embodiment 210 and similar elements have been identified with similar reference numerals having the hundreds digit "4". For example, the interpupillary distance scale 424 of the fifth embodiment 410 is similar to the interpupillary distance scale 224 of the third embodiment 210, and accordingly a detailed description of these similar features is not believed to be necessary. The differences between the fifth embodiment 410 and the third embodiment 210 are described in detail below.

In the fifth preferred embodiment, an indicator device 442 is slidably disposed on the body 411. As is best shown in FIG. 8, the indicator device 442 includes an indicator 444 which can be aligned with indicia on first and second segment height scales 426a, 426b. The first segment height scale 426a is for measurement of segment heights for glasses with frames, and the second segment height scale 426b is for measurement of segment heights for rimless glasses. Preferably, indicia 427a, 427b are provided to identify the first and second segment height scales 426a, 426b. Preferably, the segment height scales 426a, 426b are printed in different colors, preferably black for segment height scale 426a for inside frame measurements and red for segment height scale 426b for rimless outside measurements.

A stop member 446 for engaging a pair of eyeglasses is attached to the indicator device 442. In the preferred embodiment, the segment height scales 426a, 426b are located on the first principal surface 412, and the indicator device 442 is oriented such that the stop member 446 is positioned adjacent to and extends away from the second principal surface 414, opposite the segment height scales 426a, 426b.

As shown in FIG. 8, the stop member 446 preferably includes a first surface 448 which is generally rounded for engaging the inside surface of the lens-mounting portion of an eyeglass frame, thereby providing a means for measuring the height of a segment of a multi-focal lens or the vertical positioning of a progressive lens within the eyeglass frame using the first segment height scale 426a. The first surface 448 of the stop member 446 is preferably aligned with the indicator 444.

The stop member 446 also include a second, generally flat surface 450, for engaging a peripheral surface of a lens of the pair of eyeglasses, thereby providing a means for determining the height of a segment of a multi-focal lens or the positioning of a progressive lens in a pair of eyeglasses having no frame around the bottom portion of the lens using the second segment height scale 426b.

In use, the first surface 448 of the stop member 446 is engaged with the inside lens mounting surface of the eyeglass frame. The second end 418 is aligned with the level equal to the desired reference point relative to the eye of the individual and the indicator 444 is readable in conjunction with the frame indicia 427a for the first segment height scale 426a. When the second surface 450 engages a peripheral surface of a lens of the pair of eyeglasses, the second end 418 is aligned in the same manner described above, and the indicator 444 is readable in conjunction with the indicia of the second segment height scale 426b.

In the fifth preferred embodiment 410, the indicator device 442 preferably engages on the body 411 with a frictional sliding fit such that the indicator device 442 remains in a selected position until a force is applied to the indicator device 442 by the user in order to slide it upwardly or downwardly along the segment height scales 426a, 426b to measure a segment height.

As shown in FIGS. 7 and 8, preferably a clip 452 is attached to the indicator device 442 in order to allow the ruler 410 to be clipped to an object, such as a user's pocket. Preferably the clip 452 is resilient and provides a clamping force between the body 411 and the clip 452 to retain the ruler 410 in a desired position. Preferably, the indicator device 442 and the clip 452 are formed from a metallic or polymeric material, and may be molded or otherwise formed as a unitary part having the desired shape. However, it will be recognized by those skilled in the art from the present disclosure that the clip 452 may be made as a separate piece which is attached to the indicator device by a subsequent operation, such as bonding, crimping or welding.

It will be recognized by those skilled in the art from the present invention that the slidable cross member and the slidable indicator device 334, 442 of the fourth and fifth embodiments 310, 410 may be provided with a rotatable toothed wheel which engages teeth (not shown) on the body 311, 411 of the rulers 310, 410 in a rack and pinion arrangement for movement of the cross member 334 or indicator device 442 relative to the ruler bodies 311, 411. This would provide more accurate control of the sliding movement of the cross member 334 and indicator device 442.

Those skilled in the art will recognize that advertisements, or other information may be printed, etched, embossed or otherwise affixed to one or both principal surfaces 12, 14, 112, 114, 212, 214, 312, 314, 412, 414 of the rulers 10, 110, 210, 310, 410 in the areas without the interpupillary or segment height scales or within the cross members 228, 428, if desired.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An optician's ruler, comprising:
   a generally elongated body having at least first and second principal surfaces, a first end, a second end, and a longitudinal axis;
   a segment height scale on one of the at least first and second principal surfaces of the body, the segment height scale having indicia at regularly spaced intervals coinciding with standard units of measure, to permit measurement of the height of a segment of a multi-focal lens; and
   an indicator device supported by and movable with respect to the body, the indicator device including an indicator for alignment with the segment height scale indicia and a stop member for engaging a pair of eyeglasses.

2. The optician's ruler according to claim 1, wherein the stop member includes a first surface for engaging a lens mounting surface of a frame of the pair of eyeglasses.

3. The optician's ruler according to claim 2, wherein the first surface of the stop member is in alignment with the indicator.

4. The optician's ruler according to claim 1, wherein the stop member includes a second surface for engaging a peripheral surface of a lens of the pair of eyeglasses.

5. The optician's ruler according to claim 4, wherein the second surface of the stop member is in alignment with the indicator.

6. The optician's ruler according to claim 4, wherein the segment height scale is located on one principal surface and the stop member is positioned adjacent the opposing principal surface of the body.

7. The optician's ruler according to claim 1, wherein the stop member further includes a first surface for engaging a lens mounting surface of the pair of eyeglasses and a second surface for engaging a peripheral surface of a lens of the pair of eyeglasses.

8. The optician's ruler according to claim 7, wherein the segment height scale includes frame indicia and lens indicia, such that the indicator is readable in conjunction with the frame indicia when the first surface of the indicator device member engages a lens mounting surface of a frame of the pair of eyeglasses and the indicator is readable in conjunction with the lens indicia when the second surface of the indicator device member engages a peripheral surface of a lens of the pair of eyeglasses.

9. The optician's ruler according to claim 1, further comprising an interpupillary distance scale on a principal surface of the body, the interpupillary distance scale having indicia at regularly spaced intervals coinciding with standard units of measure to permit measurement of the distance between the pupils of a subject.

10. The optician's ruler according to claim 9, wherein the interpupillary distance scale and the segment height scale are on the same surface of the body.

11. The optician's ruler according to claim 10, wherein the indicator has a frictional sliding fit with the body of the ruler.

12. An optician's ruler, comprising:
a generally elongated body having a first and second principal surfaces, a first end, a second end, and a longitudinal axis extending between the ends;
a segment height scale on a principal surface of the body, the segment height scale having indicia at regularly spaced intervals coinciding with standard units of measure, to permit measurement of the height of a segment of a multi-focal lens;
an indicator device supported by and movable with respect to the body, the indicator device including an indicator for alignment with the segment height scale indicia; and
a stop member connected to a principal surface of the body for engaging a pair of eyeglasses.

13. The optician's ruler according to claim 12, wherein the stop member is on the same end as the segment height scale.

14. The optician's ruler according to claim 12, wherein the segment height scale is located proximate to one longitudinal end of the body and the stop member further includes a first surface for engaging a lens mounting surface of the pair of eyeglasses.

15. The optician's ruler according to claim 12, wherein the stop member further includes a second surface for engaging a peripheral surface of a lens of the pair of eyeglasses.

16. The optician's ruler according to claim 12, wherein the member further includes a first surface for engaging a lens mounting surface of the pair of eyeglasses and a second surface for engaging a peripheral surface of a lens of the pair of eyeglasses.

17. The optician's ruler according to claim 12, wherein the indicator device includes a cross member wider than the body.

18. The optician's ruler according to claim 12, wherein the member and the segment height indicia are on opposite principal surfaces of the body.

19. The optician's ruler according to claim 12, further comprising an interpupillary distance scale on a principal surface of the body, the interpupillary distance scale having indicia at regularly spaced intervals coinciding with standard units of measure to permit measurement of the distance between the pupils of a subject.

20. The optician's ruler according to claim 19, wherein the interpupillary distance scale and the segment height scale are on the same surface of the body.

21. The optician's ruler according to claim 20, wherein the indicator device has a frictional sliding fit with the body of the ruler.

* * * * *